(12) United States Patent
Kuo et al.

(10) Patent No.: US 9,098,894 B2
(45) Date of Patent: Aug. 4, 2015

(54) DEFECT DETERMINATION IN INTEGRATED CIRCUIT MANUFACTURING PROCESS

(71) Applicant: Taiwan Semiconductor Manufacturing Company, Ltd., Hsin-Chu (TW)

(72) Inventors: Min-Sung Kuo, Zhubei (TW); Chiun-Chieh Su, Hsin-Chu (TW); To-Yu Chen, Tu-Ku Town (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 154 days.

(21) Appl. No.: 13/757,592

(22) Filed: Feb. 1, 2013

(65) Prior Publication Data

US 2014/0219543 A1 Aug. 7, 2014

(51) Int. Cl.
*G06K 9/00* (2006.01)
*G06T 7/00* (2006.01)
*G01N 21/956* (2006.01)
*H01L 21/66* (2006.01)

(52) U.S. Cl.
CPC .......... *G06T 7/001* (2013.01); *G01N 21/95607* (2013.01); *H01L 22/12* (2013.01); *H01L 22/20* (2013.01); *G06T 2207/30148* (2013.01)

(58) Field of Classification Search
USPC ......... 382/141, 145, 146, 147, 149, 150, 152; 348/86, 87, 92, 126
See application file for complete search history.

(56) References Cited

U.S. PATENT DOCUMENTS

| | | | | |
|---|---|---|---|---|
| 7,065,239 B2 * | 6/2006 | Maayah et al. | ............... | 382/145 |
| 8,090,187 B2 * | 1/2012 | Sakai et al. | ................... | 382/141 |
| 8,150,140 B2 * | 4/2012 | Kitamura et al. | ............. | 382/141 |
| 8,209,135 B2 * | 6/2012 | Funakoshi et al. | ............. | 702/35 |
| 8,379,196 B2 * | 2/2013 | Kamiyama et al. | ........ | 356/237.2 |
| 8,581,976 B2 * | 11/2013 | Kurihara et al. | ............. | 348/126 |
| 8,670,115 B2 * | 3/2014 | Miyoshi et al. | ............ | 356/237.1 |

* cited by examiner

*Primary Examiner* — Wesley Tucker
(74) *Attorney, Agent, or Firm* — Slater & Matsil, L.L.P.

(57) ABSTRACT

A method includes inspecting a wafer to find a first potential defect having a first wafer coordinate, and capturing a patch image of the first potential defect from the wafer. The patch image is compared with patterns of a wafer representation to find a first layout coordinate of a location in the wafer representation, wherein the location in the wafer representation corresponds to a location of the first potential defect in the wafer. A reference feature in the wafer representation is selected, wherein the reference feature in the wafer representation has a second layout coordinate. A coordinate difference between the first layout coordinate and the second layout coordinate is calculated. The coordinate difference is subtracted from the first wafer coordinate to calculate a second wafer coordinate of a reference feature in the wafer, wherein the reference feature in the wafer representation corresponds to the reference feature in the wafer.

20 Claims, 6 Drawing Sheets

DEFECT DETERMINATION IN INTEGRATED CIRCUIT MANUFACTURING PROCESS

BACKGROUND

The manufacturing of integrated circuits involves many process steps. After each of the manufacturing process steps, the wafers may need to be inspected to find defects, so that the yield of the respective process step may be determined. When the number of defects is great enough, and the yield is no longer acceptable, the manufacturing process needs to be halted, and steps need to be taken to improve the yield.

The determination of the yield typically includes two steps. In the first step, a wafer is inspected using an inspection tool, wherein dies in the wafer are compared so that potential defects may be found. The coordinates of the potential defects are recorded. In the second step, the wafer on which the potential defects are found is loaded on a review tool. The potential defects are reviewed manually to determine whether the potential defects are real defects or not.

The reviewing of the potential defects is typically time consuming. One of the reasons is that the inspection tool and the review tool have variations in determining the coordinates of the potential defects. The variations may range from several microns to about one hundred microns. As a result, in the review process, when no defect is found at a location of a potential defect, there may be two possible reasons. The first reason is that the potential defect is not an actual defect. This may be caused since the inspection tool is too sensitive and wrongfully identifies a non-defect as a defect. The second reason is that due to the variations in the inspection tool and/or the review tool, on the review tool, a wrong location is reviewed, while the actual defect is at a nearby location. To exclude the second possibility, the operator of the review tool has to search the nearby locations of the potential defect until either the defect is found, or until a nearby region that is large enough is searched, and no defect is found. Due to the effort required for the manual search of the possibility defects, the reviewing process is lengthy.

BRIEF DESCRIPTION OF THE DRAWINGS

For a more complete understanding of the embodiments, and the advantages thereof, reference is now made to the following descriptions taken in conjunction with the accompanying drawings, in which.

DETAILED DESCRIPTION OF ILLUSTRATIVE EMBODIMENTS

Figure 1:
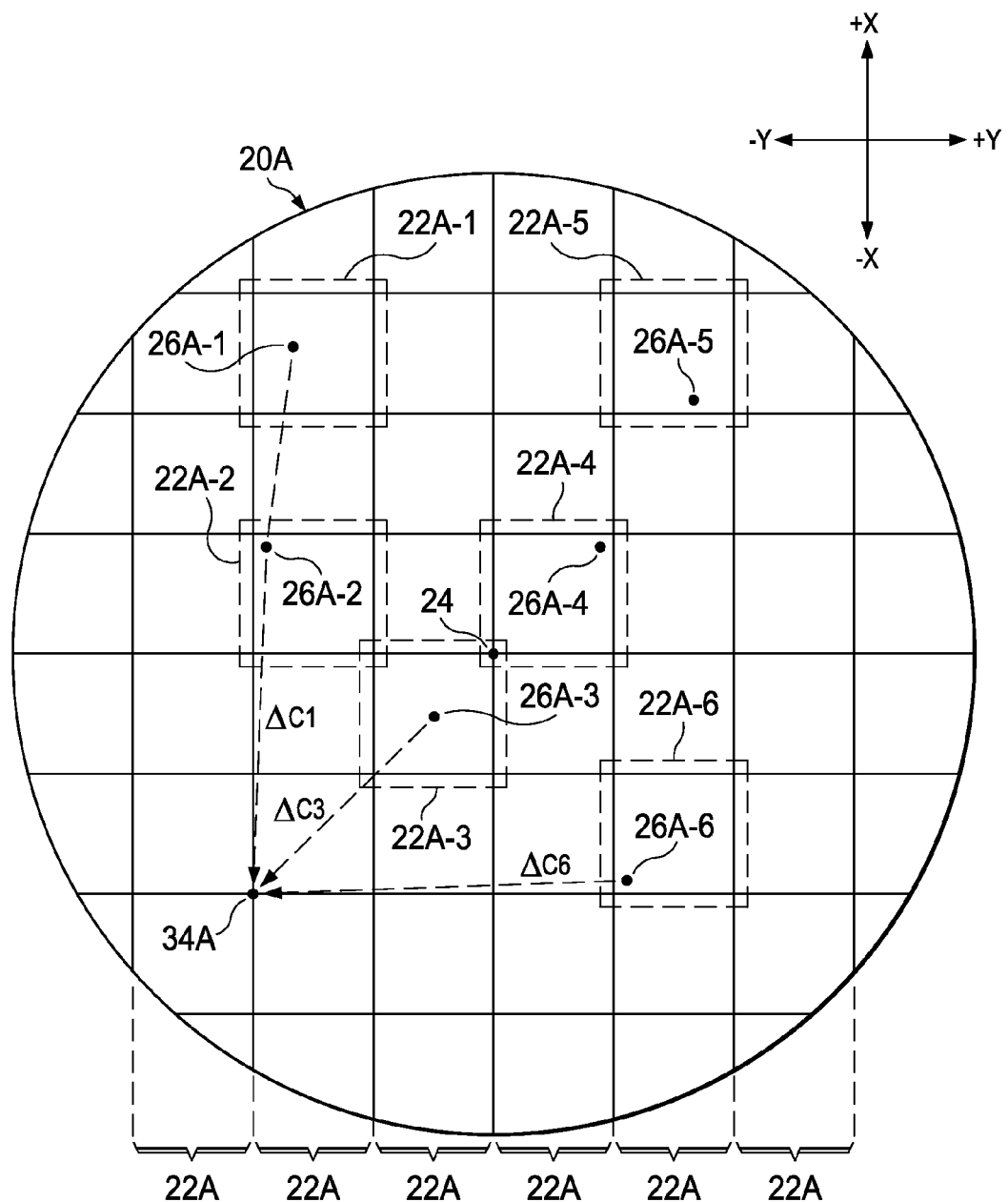
FIG. 1 illustrates a top view of a wafer, in which potential defects are found in accordance with exemplary embodiments.

The making and using of the embodiments of the disclosure are discussed in detail below. It should be appreciated, however, that the embodiments provide many applicable concepts that can be embodied in a wide variety of specific contexts. The specific embodiments discussed are illustrative, and do not limit the scope of the disclosure.

A method of finding and verifying defects on wafers is provided in accordance with various exemplary embodiments. The variations and the operation of the method are discussed. Throughout the various views and illustrative embodiments, like reference numbers are used to designate like elements. Throughout the description, letters "A" or "B" may follow reference numerals, wherein the reference numerals with letter "A" represent features in a physical wafer, and reference numerals with letter "B" represent features in a wafer representation, which includes the layout of the wafer. The wafer representation is thus not a physical wafer. Furthermore, when a first point (or feature) in the wafer is in the same relative position as a second point (or feature) in the wafer representation, the first point/feature and the second point/feature are referred to as being "corresponding" to each other. For example, a center die in the wafer corresponds to a center die in the wafer representation, and a corner of the center die in the wafer corresponds to the corner of the center die in the wafer representation.

Figure 6:
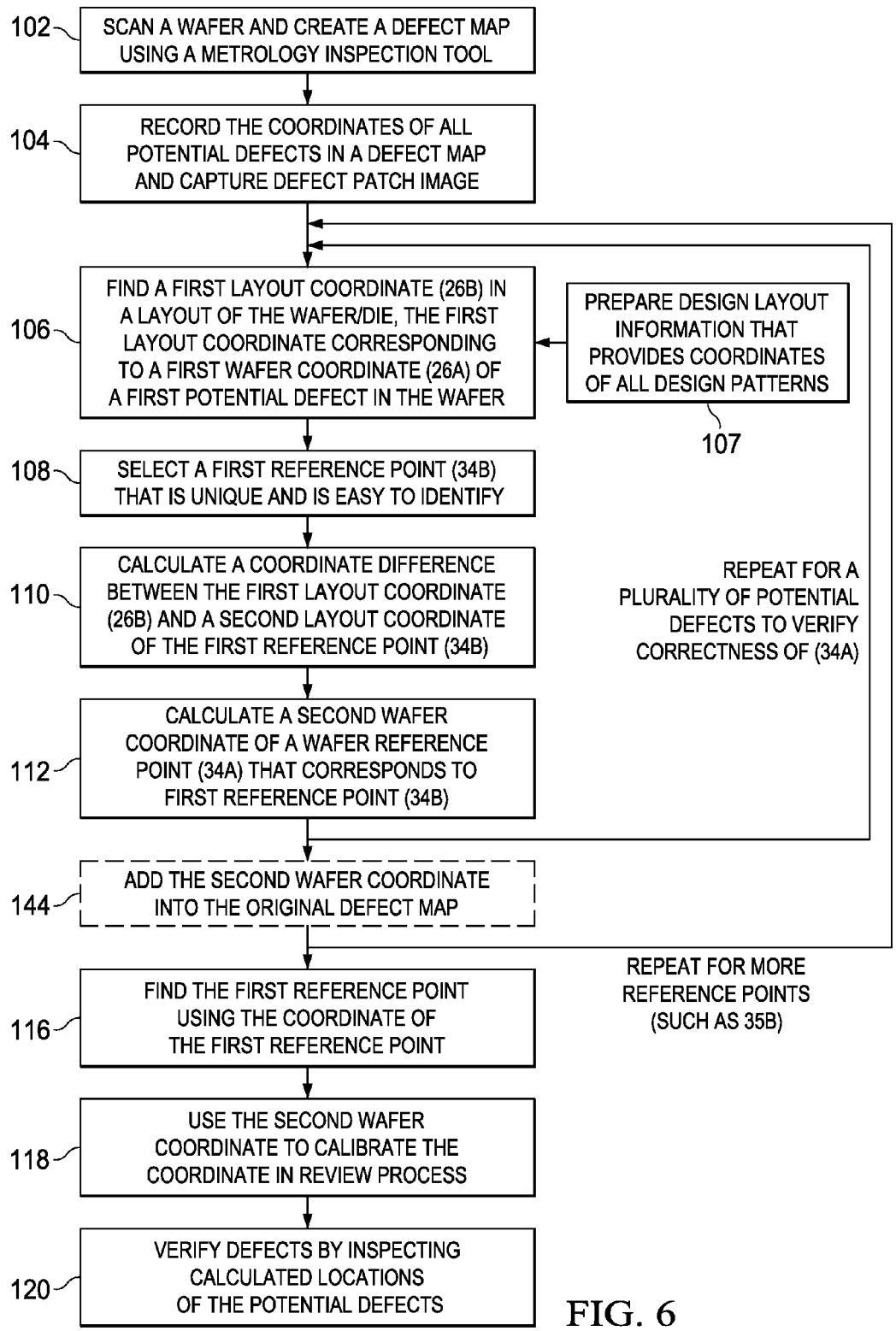
FIG. 6 illustrates a process flow in accordance with exemplary embodiments.

FIG. 6 illustrates a process flow for finding and verifying defects on a wafer in accordance with exemplary embodiments, wherein the methods in accordance with the exemplary embodiments are discussed referring to the process flow in FIG. 6. In step 102, an inspection (wafer scanning) is performed on wafer 20A (FIG. 1). FIG. 1 also shows a defect map, which illustrates potential defects and their positions in wafer 20A. During the inspection, the features in wafer 20A are scanned and measured, and potential defects in wafer 20A are found. FIG. 1 schematically illustrates a top view of wafer 20A, which includes a plurality of dies 22A (illustrated as squares) therein. The plurality of dies 22A has layouts that are identical to each other. The manufacturing of integrated circuits in wafer 20A at this time may be, or may not be finished yet. The surface features (such as the illustrated features 32 in FIG. 2) in wafer 20A may be any features including, and not limited to, dielectric regions, polysilicon features, metal lines, metal vias, contact plugs, and the like. The defects in accordance with the exemplary embodiments may thus be the defects in the surface features that can be measured at this time.

In step 102 in FIG. 6, the inspection is performed on wafer 20A (FIG. 1) using an inspection tool (not shown). In some embodiments, the inspection tool comprises a metrology tool which can measure the dimensions, shapes, and/or the layouts of the surface features. For example, the inspection tool may be one of "Vanquish 29xx," "Firebird 28xx," "PUMA 91xx," "PUMA 95xx," and "PUMA 98xx," manufactured by KLA Tencor Inc., or one of "UVision5" and "UVision6" manufactured by Applied Materials, Inc. The inspection tool is configured to measure the defects on dies 22A. In some embodiments, the inspection tool finds the defects by comparing the surfaces features on each of the dies 22A with the corresponding features on other dies 22A. Since dies 22A should have identical layouts of the surface features, when a mismatch is found between the corresponding features on two dies 22A, a defect may be found. Throughout the description, the defects found by the inspection tool are referred to as potential defects since they may be real defects, or may not be real defects either. The potential defects may include, and are not limited to, connections that should exist but undesirably broken, undesirable bridges between features that should be disconnected, and the like. In FIG. 1, potential defects are shown as 26A (including 26A1 through 26A6) in some exemplary embodiments.

All potential defects 26A found by the inspection tool are recorded (step 104 in FIG. 6) to form a defect map, which is also shown in FIG. 1. The coordinate of each of the potential defects 26A is recorded in the defect map. In some embodiments, the inspection tool adopt a coordinate system (referred to as a wafer coordinate system) for wafer 20A, wherein the coordinate system includes an X coordinate and a Y coordinate, and wherein a coordinate may be expressed as (X value, Y value). One point of wafer 20A may be selected as the origin of the wafer coordinate system. In accordance with some exemplary embodiments, the wafer coordinate system may select a center die as an origin die, and one point in the origin die as the origin of the entire wafer coordinate system. For example, in FIG. 1, the left bottom corner of die 22A-4 may be selected as origin 24 of the wafer coordinate system, and the coordinates of all points on wafer 20A is determined with respect to origin 24. The coordinate of each of the potential defects 26A is associated with which of dies 22A the potential defect is in, and the relative (position) coordinate of the defect in the respective die. For example, a coordinate of a potential defect may be recorded as (520.1, −345.3) with respect to wafer origin 24, and/or recorded as (12.3, 21.2) with respect to the left bottom corner of die (−3, −2), wherein (−3, −2) indicates that die (−3, −2) is in the third column to the −X direction counted from origin die 22A-4, and is in the second row in −Y direction counted from origin die 22A-4.

In some embodiments, there may be zero to many potential defects found during step 102 in FIG. 6. FIG. 1 illustrates some exemplary potential defects 26A, namely 26A-1 through 26A-6. The respective dies including potential defects 26A-1 through 26A-6 are dies 22A-1 through 22A-6, respectively. The actual number of potential defects may be more or fewer than illustrated.

Figure 2:
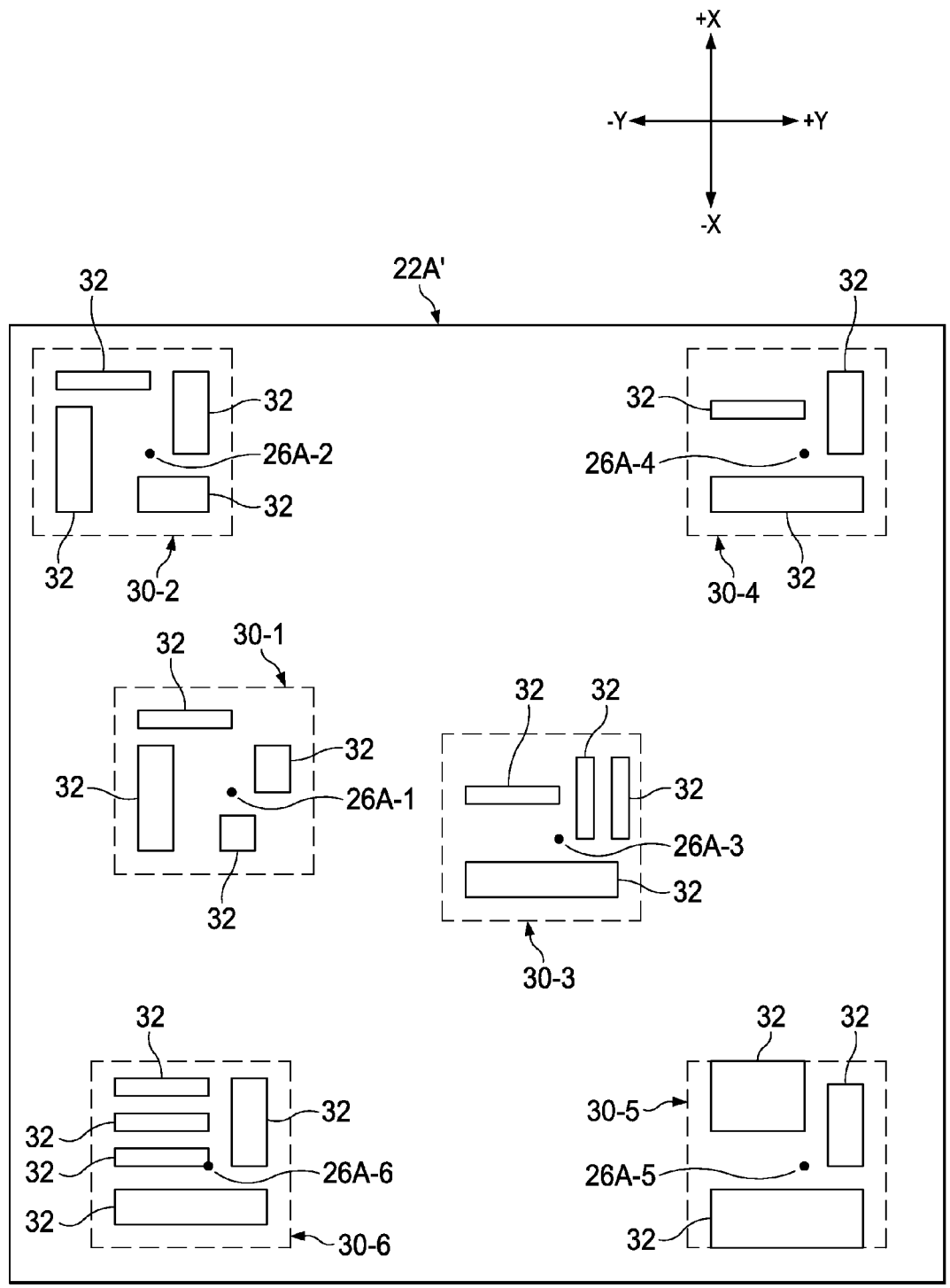
FIG. 2 illustrates a die, wherein the potential defects and the respective patch images are shown in the same die.

A patch image may be captured (step 104 in FIG. 6) for each of potential defects 26A, wherein the patch image may be captured by a camera. FIG. 2 schematically illustrates patch images 30 (including 30-1 through 30-6) for potential defects 26A-1 through 26A-6, respectively. The patch images 30 include the shapes and the layouts of regions having the respective potential defects therein. Patch images 30 may have sizes ranging from, for example, 1 μm×1 μm to 5 μm×5 μm, although patch images 30 may be larger or smaller. In FIG. 2, all potential defects 26A and the respective patch images 30 are illustrated in a same die 22A' (which has the same layout as all of dies 22A in FIG. 1), although in reality, potential defects 26A and the respective patch images 30 are in different dies. The relative position of each of potential defects 26A in the illustrated die 22A' with respect to the receptive die origin is the same as the relative position of the respective potential defects 26A in FIG. 1. For example, assume in FIG. 1, potential defect 26A-6 has coordinate (5.1, 5.2) with respect to the origin of die 22A-6, then potential defect 26A-6 in FIG. 2 also has coordinate (5.1, 5.2) with respect to the origin of die 22A', and so are the same for other potential defects 26A.

Figure 3:
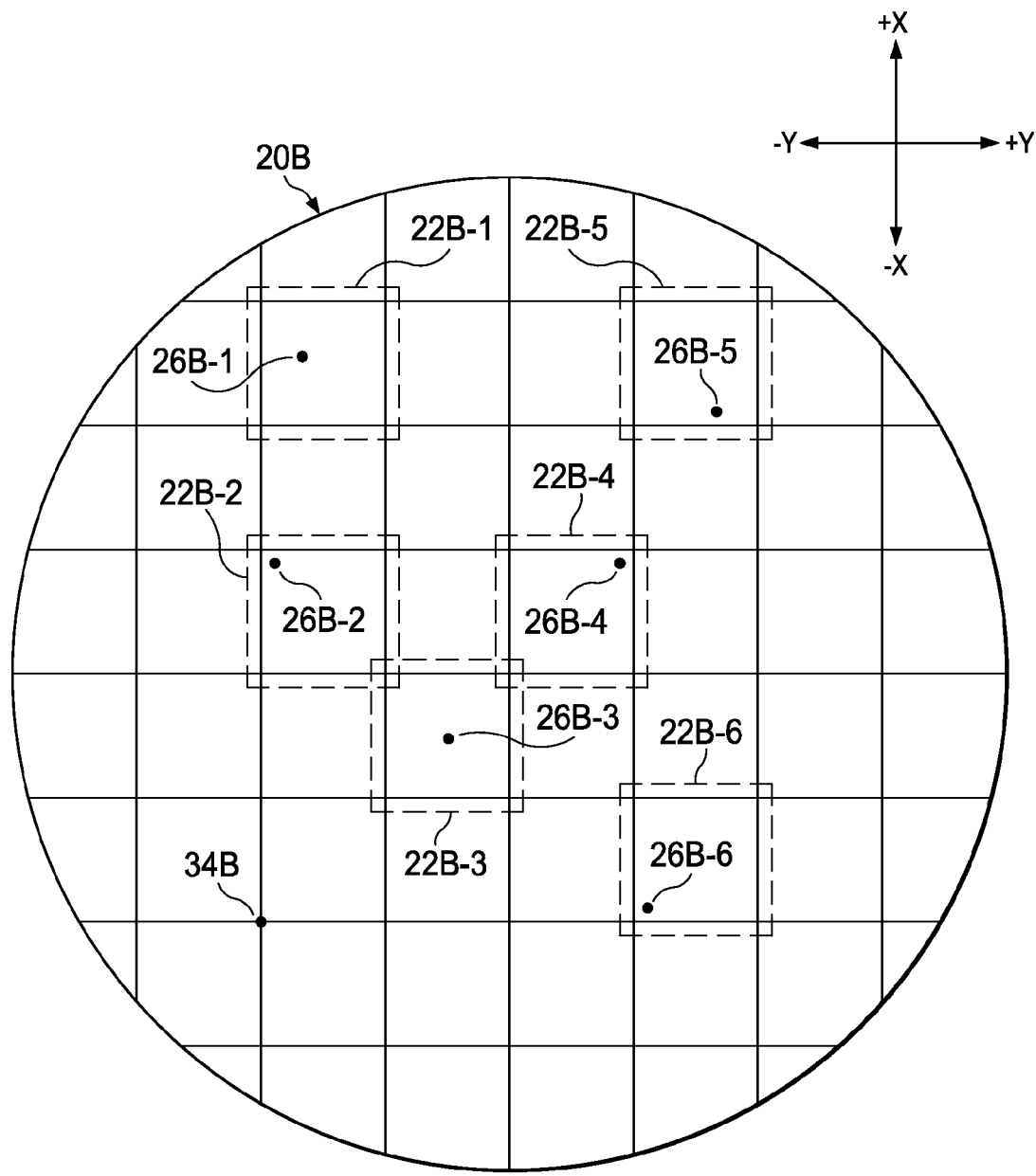
FIG. 3 illustrates an exemplary layout of a wafer representation in accordance with exemplary embodiments.

Surface features 32 in FIG. 2 have a layout. Before the manufacturing of integrated circuits, the design layout (including the coordinates) of all patterns in the integrated circuits are prepared (step 107 in FIG. 6). Potential defects 26A in FIG. 1 are defects in surface features in FIG. 2. Surface features 32 are formed using a lithography mask (not shown). The layout of surface features 32 is reproduced from a layout file, which may be saved in a Graphic Data System (GDS) format. The layout file may be searched and compared using a computer. FIG. 3 illustrates an exemplary wafer representation 20B including the layout of wafer 20A, including the layout of surface features 32. The layout is in a GDS file in the GDS format or any other data format that may represent layouts. Wafer representation 20B also includes die representations 22B, which are the representation of dies 22A (FIG. 1). Die representations 22B also have the same layouts as dies 22A. Wafer representation 20B has a coordinate system (referred to as a layout coordinate system hereinafter), which has the same scale as the wafer coordinate system in FIG. 1. Corresponding points in the wafer coordinate system and the layout coordinate system, however, may have different coordinate values, although their coordinates may also be the same.

Next, as shown as step 106 in FIG. 6, the patch images 30 (FIG. 2) are compared to the layout in wafer representation 20B (FIG. 3) to look for the coordinates of potential defects 26A (FIG. 1) in the layout coordinate system. Wafer representation 20B may be stored in the GDS file, and include the same layout of features 32 (FIG. 2) as wafer 20A. In some exemplary embodiments, assuming potential defect 26A-1 is looked for, the layout of patch image 30-1 is compared to the layout in wafer 20A. It is appreciated that since die representations 22B are identical to each other, the comparison may be performed by comparing patch image 30A-1 through 30A-6 with the layout of a same one of any of die representations 22B. When a region in wafer representation 20B has a layout same as the layout of features 32 in patch image 30-1, then it is expected the region of patch image 30-A corresponds to the region that is found in wafer representation 20B. It is assumed that at the positions (in wafer representation 20B) corresponding to the positions of potential defects 26A (in wafer 20A), there are virtual potential defects 26B, which correspond to potential defects 26A-1 through 26A-6, respectively. Virtual potential defects 26B including 26B-1 through 26B-6 are thus added into wafer representation 20B in order to perform subsequent steps, wherein virtual potential defects 26B-1 through 26B-6 correspond to potential defects 26A-1 through 26A-6, respectively.

Figure 4:
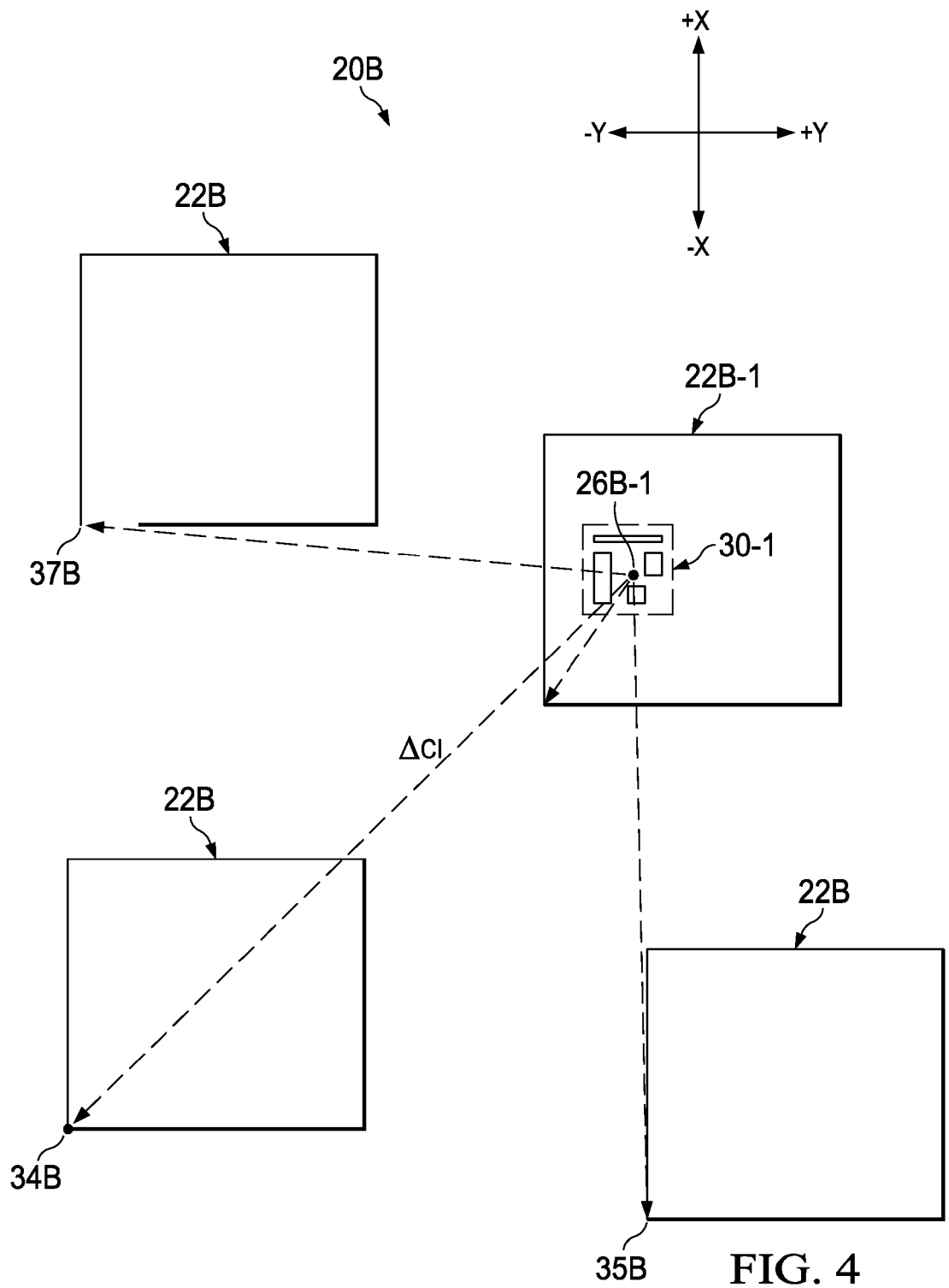
FIG. 4 illustrates a selected reference feature in the wafer representation, and the coordinate difference between the selected reference feature and one of the potential defects in the wafer representation.

Next, referring to step 108 in FIG. 6, a reference point 34B (which may also be a reference feature) in wafer representation 20B is selected, and is shown in FIG. 4. FIG. 4 schematically illustrates the layout of portions of wafer representation 20B. Reference point 34B may also be a reference feature, and hence is referred to as reference feature 34B hereinafter. Reference feature 34B is a unique feature that is easy to identify. Reference feature 34B is also unique enough that other features will not be wrongfully identified as reference feature 34B. For example, one of the four corners of a selected one of die representations 22B (such as the center die) may be selected as reference feature 34B, although other reference features may be selected. Furthermore, alignment marks with a unique pattern may be formed to act as reference feature 34B. When the corner of a die is selected as reference feature 34B, since the corner may be the cross point of two sides of a seal ring of the die, and the two sides are straight sides having the length substantially equal to the length of the respective side of the die, it is easy to identify reference feature 34B.

Referring to FIG. 4, with reference feature 34B selected, since the coordinates of reference feature 34B in the layout coordinate system is known, the coordinate difference $\Delta C1$ between potential defect 26B-1 and reference feature 34B is calculated (step 110 in FIG. 6). For example, assuming the coordinate of potential defect 26B-1 in the layout coordinate system is (130, 131), and the coordinate of reference feature 34B in the layout coordinate system is (40, 42), the coordinate difference $\Delta C1$ between points 26B-1 and 34B is (90, 89).

Figure 5:
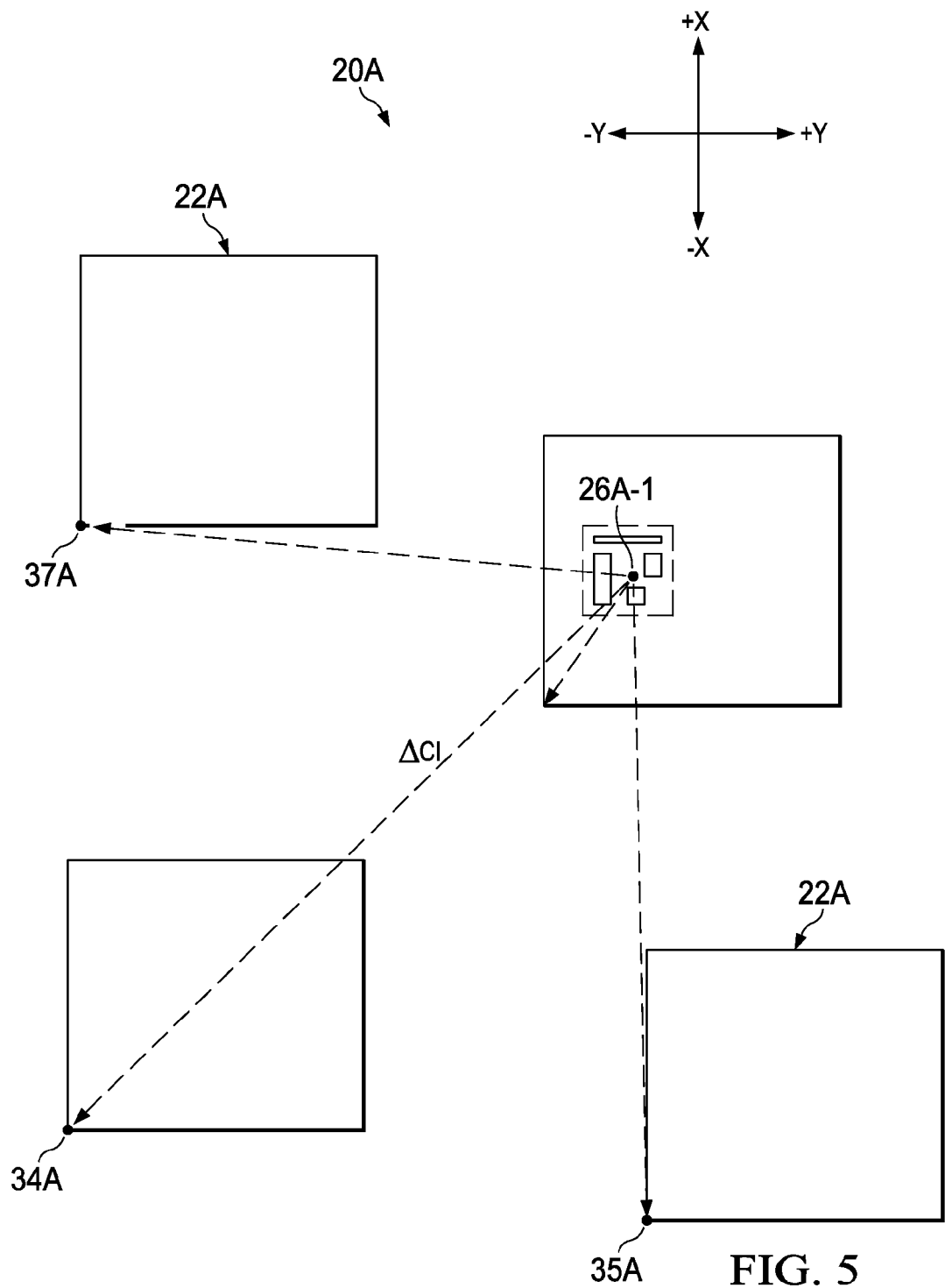
FIG. 5 illustrates the selected reference feature in a wafer, and the coordinate difference between the selected reference feature and one of the potential defects in the wafer.

Reference feature 34B in FIG. 4 has a corresponding reference feature 34A in wafer 20A, which is shown in FIG. 5. FIG. 5 schematically illustrates the layout of portions of wafer 20A, which portions correspond to the portions shown in FIG. 4. Reference features 34A and 34B are at the same relative positions with respect to their own wafer 20A and wafer representation 20B, respectively. Since points 26B-1 and 34B in FIG. 4 have coordinate difference ΔC1 (for example, (90, 89)), points 26A-1 and reference feature 34A in FIG. 5 must have coordinate difference equal to ΔC1, which is (90, 89) in this example, and hence the coordinate of reference feature 34A (FIG. 5) can be calculated (step 112 in FIG. 6). Accordingly, assuming potential defect 26A-1 (FIG. 5) has the wafer coordinate (100, 95), then reference feature 34A must have coordinate wafer (100-90, 95-89), which is (10, 6). Throughout the description, reference feature 34A is also referred to as a virtual defect since in the subsequent reviewing of wafer 20A in FIG. 1, reference feature 34A is looked for and reviewed (using the review tool) similar to the review of potential defects. Alternatively stated, the virtual defect 34A is added into the defect map (FIG. 1) that is created in step 102 (FIG. 6), which adding step of the virtual defect 24A is shown as step 114 in FIG. 6. The coordinate differences between other potential defects 26A in FIG. 1 and reference feature 34A can also be calculated using the newly calculated wafer coordinate (10, 6) of reference feature 34A by subtracting the coordinate (such as (10, 6)) of reference feature 34A from the wafer coordinates of potential defects 26A-2 through 26A-6. The coordinate differences of potential defects 26A-2 through 26A-6 are referred to as ΔC2 through ΔC6, respectively. For the clarity of FIG. 1, coordinate differences ΔC1, ΔC3, and ΔC6 are illustrated in FIG. 1, and ΔC2, ΔC4, and ΔC5 are not shown.

Through steps 106, 108 and 110 in FIG. 6, the wafer coordinate of reference feature 34A (FIG. 5) in the wafer coordinate system is calculated. Accordingly, when wafer 20A in FIG. 1 is loaded on a review tool (not shown), which may be an optical microscope or an electron microscope, the wafer coordinate (such as (10, 6)) of reference feature 34A is used by the operator of the review tool to search for reference feature 34A, which is unique enough and can be easily found. Upon finding the reference feature 34A (step 116 in FIG. 6) through the microscope, the microscope may move its review region from the starting point 34A by a distance equal to the coordinate difference ΔC1, for example, (90, 89). The destination point should be the position of potential defect 26A-1. If there is a defect found at the destination point, then the existence of potential defect 26A-1 is verified, and potential defect 26A-1 is confirmed to be a real defect (step 120 in FIG. 6). If there is no defect found at the destination point, then it is verified that potential defect 26A-1 is not a real defect (also step 120 in FIG. 6). Accordingly, the operator of the review tool does not need to search the nearby region of the destination point to verify the non-existence of the defect. Using the similar steps as verifying potential defect 26A-1, all other defects 26A in wafer 20A may be confirmed (step 120 in FIG. 6).

The review tool may have a coordinate variation, which variation may be caused by the difference between the inspection tool and the review tool. Due to the coordinate variation, all the points/features in the coordinate system of the review tool may be shifted slightly from their corresponding points/features in the coordinate system of the inspection tool. This causes reference feature 34A (FIG. 1) to be shifted from the calculated coordinate (10, 6) by an offset when the review tool is used to review reference feature 34A. Such offset may be calibrated (step 118) in FIG. 6. For example, the operator of the review tool finds that reference feature 34A is not at coordinate (10, 6). The operator then searches the surrounding regions of coordinate (10, 6), and finds that reference feature 34A (which may be a die corner) is at (15, 12). It is then known that the offset is (15-10, 12-6), which is (5, 6). The determination of the offset is referred to as the calibration of the review tool (step 118 in FIG. 6). Therefore, the offset (5, 6) is used to offset the variation between the review tool and the inspection tool. When potential defect 26A-1 is verified, the offset is added to the coordinate difference ΔC1 (90, 89) to obtain (95, 95), and point (95, 95) is verified for the existence of potential defect 26A-1. Similarly, all other potential defects 26A-2 through 26-6 can be verified (step 120 in FIG. 6) similar to the verification of 26A-1 by moving from the actual coordinate (15, 12), rather than (10, 6), of reference feature 34A by distances equal to coordinate differences ΔC2 through ΔC6 (with ΔC1, ΔC2, and ΔC6 shown in FIG. 1, and others not shown), respectively.

Referring back to FIG. 6, although in FIG. 4, one potential defect 26A may be used in steps 106, 108, 110, and 112 to find the wafer coordinate of reference feature 34A. Errors may occur in these steps, and the coordinate (10, 6) of reference feature 34A in the wafer coordinate system may be incorrect or inaccurate. Accordingly, as shown in FIG. 6, steps 106, 108, 110, and 112 may be repeated for some or all of other patch images 30-2 through 30-6 (FIG. 2), with one wafer coordinate calculated for reference feature 34A using each of patch images 30-2 through 30-6. The respective step is illustrated in FIG. 6 using an arrow pointing from the output end of step 112 back to the input end of step 106. If all coordinates calculated for reference feature 34A using all patch images 30-1 through 30-6 are the same, then it is verified that the wafer coordinate of reference feature 34A is correct. Otherwise, if there is a discrepancy between the calculated wafer coordinates of reference feature 34A, further verification is needed to determine which of the calculated wafer coordinates is correct. Generally, the more patch images 30 are used to repeat steps 106, 108, 110, and 112, the more confidence can be built upon the correctness of the calculated wafer coordinate of reference feature 34A. In some embodiments, five to ten patch images are used to calculate and verify the wafer coordinate of reference feature 34A.

Referring back to FIG. 6 again, steps 106, 108, 110, 112, and 114 may be repeated to calculate the coordinate of reference feature 35A (FIG. 5). The respective step is illustrated in FIG. 6 using an arrow pointing from the output end of step 114 back to the input end of step 106. In the respective steps, a second reference feature 35B (FIG. 4) may be selected, and. Reference feature 35A corresponds to reference feature 35B in FIG. 4. The second reference feature 35A may be used similar to the usage of reference feature 34A. Furthermore, more references points such as 37B (FIG. 4) and the respective reference feature 37A (FIG. 5) may be selected, calculated, and used similar to reference features 34B/35B and 34A/35A. With more than one reference features 34A/35A/37A, more accurate calibration may be performed in the review step.

In accordance with some embodiments, a method includes inspecting a wafer to find a first potential defect having a first wafer coordinate, and capturing a patch image of the first potential defect from the wafer. The patch image is compared with patterns of a wafer representation to find a first layout coordinate of a location in the wafer representation, wherein the location in the wafer representation corresponds to a location of the first potential defect in the wafer. A reference feature in the wafer representation is selected, wherein the reference feature in the wafer representation has a second layout coordinate. A coordinate difference between the first layout coordinate and the second layout coordinate is calculated. The coordinate difference is subtracted from the first wafer coordinate to calculate a second wafer coordinate of a reference feature in the wafer, wherein the reference feature in the wafer representation corresponds to the reference feature in the wafer.

In accordance with other embodiments, a method includes inspecting a wafer to generate a defect map, wherein the defect map comprises a plurality of potential defects found during the step of inspecting the wafer. The plurality of potential defects has wafer coordinates. The plurality of potential defects further includes a first potential defect having a first wafer coordinate. Layout coordinates of the plurality of potential defects are found from a GDS file having layouts of the wafer, wherein the layout coordinates are coordinates of points corresponding to positions of the plurality of potential defects. A reference feature in the GDS file is selected. A second wafer coordinate of the reference feature in the wafer is calculated. In the step of calculating, the wafer coordinates of the plurality of potential defects and the layout coordinates are used as parameters.

In accordance with yet other embodiments, a method includes inspecting a wafer to generate a defect map, wherein the defect map includes a potential defect found during the step of inspecting the wafer, and wherein the potential defect has a first wafer coordinate. The method further includes determining a second wafer coordinate of a unique feature in the wafer, calculating a coordinate difference between the first wafer coordinate and the second wafer coordinate, and reviewing the wafer. The step of reviewing includes pointing to the second wafer coordinate, moving from the second wafer coordinate by the coordinate difference to point to a destination point, and inspecting a region of wafer comprising the destination point to determine a validity of the potential defect.

Although the embodiments and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized according to the disclosure. Accordingly, the appended claims are intended to include within their scope such processes, machines, manufacture, compositions of matter, means, methods, or steps. In addition, each claim constitutes a separate embodiment, and the combination of various claims and embodiments are within the scope of the disclosure.

What is claimed is:

1. A method comprising:
   inspecting a wafer to find a first potential defect, wherein the first potential defect has a first wafer coordinate;
   capturing a patch image of the first potential defect from the wafer;
   comparing the patch image with patterns of a wafer representation to find a first layout coordinate of a location in the wafer representation, wherein the location in the wafer representation corresponds to a location of the first potential defect in the wafer, and wherein the wafer representation has a layout of the wafer;
   selecting a reference feature in the wafer representation, wherein the reference feature in the wafer representation has a second layout coordinate;
   calculating a coordinate difference between the first layout coordinate and the second layout coordinate; and
   subtracting the coordinate difference from the first wafer coordinate to calculate a second wafer coordinate of a reference feature in the wafer, wherein the reference feature in the wafer representation corresponds to the reference feature in the wafer.

2. The method of claim 1 further comprising:
   reviewing the wafer comprising:
      finding the reference feature in the wafer;
      moving from the reference feature in the wafer by the coordinate difference to a destination point; and
      reviewing the destination point to find the first potential defect.

3. The method of claim 2 further comprising a calibrating step comprising:
   pointing to a point having the second wafer coordinate;
   recording an actual wafer coordinate of the reference feature; and
   calculating an offset between an actual wafer coordinate of the reference feature and the second wafer coordinate.

4. The method of claim 1, wherein the wafer representation is comprised in a Graphic Data System (GDS) file, with patterns of features inspected in the step of inspecting the wafer saved in the GDS file.

5. The method of claim 1, wherein during the step of inspecting the wafer, a second potential defect is found and having a third wafer coordinate, and wherein the method further comprises:
   capturing an additional patch image of the second potential defect;
   comparing the additional patch image with patterns of the wafer representation to find a third layout coordinate of a point corresponding to a location of the second potential defect;
   calculating an additional coordinate difference between the third layout coordinate and the second layout coordinate; and
   subtracting the additional coordinate difference from the third wafer coordinate to calculate a fourth wafer coordinate of the reference feature in the wafer.

6. The method of claim 5 further comprising comparing the second wafer coordinate with the fourth wafer coordinate to verify a correctness of the second wafer coordinate.

7. The method of claim 1, wherein the step of inspecting the wafer is performed by a metrology tool.

8. A method comprising:
   inspecting a wafer to generate a defect map, wherein the defect map comprises a plurality of potential defects found during the step of inspecting the wafer, wherein the plurality of potential defects has wafer coordinates, and wherein the plurality of potential defects comprises a first potential defect having a first wafer coordinate;
   finding layout coordinates of the plurality of potential defects from a Graphic Data System (GDS) file having layouts of the wafer, wherein the layout coordinates are coordinates of points corresponding to positions of the plurality of potential defects;
   selecting a reference feature in the GDS file; and
   calculating a second wafer coordinate of the reference feature in the wafer, wherein in the step of calculating, the wafer coordinates of the plurality of potential defects and the layout coordinates are used as parameters.

9. The method of claim 8, wherein a point in the GDS file corresponding to the first potential defect has a first layout coordinate, and wherein the step of calculating the second wafer coordinate comprises:
   finding a coordinate difference between the first layout coordinate and a second layout coordinate of the reference feature in the GDS file; and
   calculating the second wafer coordinate by using the coordinate difference and the first wafer coordinate.

10. The method of claim 9, wherein the step of calculating the second wafer coordinate comprises subtracting the coordinate difference from the first wafer coordinate.

11. The method of claim 9, wherein the steps of finding the coordinate difference and calculating the second wafer coordinate are performed for each of the plurality of potential defects.

12. The method of claim 8, wherein the reference feature comprises a corner of a die representation in the GDS file.

13. The method of claim 8 further comprising adding a virtual defect into the defect map, wherein the virtual defect has the second wafer coordinate.

14. The method of claim 8, wherein the step of inspecting the wafer comprises comparing dies in the wafer, wherein differences between the dies are recorded as the plurality of potential defects.

15. A method comprising:
   inspecting a wafer to generate a defect map, wherein the defect map comprises a potential defect found during the step of inspecting the wafer, and wherein the potential defect has a first wafer coordinate;
   determining a second wafer coordinate of a unique feature in the wafer;
   calculating a coordinate difference between the first wafer coordinate and the second wafer coordinate; and
   reviewing the wafer, wherein the step of reviewing comprises:
      pointing to the second wafer coordinate;
      moving from the second wafer coordinate by the coordinate difference to point to a destination point; and
      inspecting a region of wafer comprising the destination point to determine a validity of the potential defect.

16. The method of claim 15, wherein the unique feature comprises a die corner in the wafer.

17. The method of claim 15, wherein the step of calculating the coordinate difference comprises:
   finding from a layout file a first layout coordinate of a point corresponding to the potential defect, wherein the layout file comprises a layout of the wafer;
   selecting a unique feature in the GDS file, wherein the unique feature in the GDS file corresponds to the unique feature in the wafer; and
   calculating the coordinate difference by calculating a difference between the first layout coordinate and a second layout coordinate of the unique feature in the GDS file.

18. The method of claim 15 further comprising performing a calibration comprising:
   finding an actual wafer coordinate of the unique feature in the wafer; and
   calculating an offset equal to a difference between the actual wafer coordinate and the second wafer coordinate.

19. The method of claim 18, wherein the coordinate difference is calculated by combining the coordinate difference with the offset.

20. The method of claim 15, wherein the step of reviewing the wafer is performed using a microscope.

* * * * *